United States Patent [19]

Kamienski et al.

[11] 3,954,894

[45] May 4, 1976

[54] ORGANOTRILITHIUM POLYMERIZATION INITIATORS

[75] Inventors: Conrad W. Kamienski; Robert C. Morrison, both of Gastonia, N.C.

[73] Assignee: Lithium Corporation of America, New York, N.Y.

[22] Filed: May 18, 1973

[21] Appl. No.: 361,467

[52] U.S. Cl. .................. 260/665 R; 252/431 L; 260/680 B
[51] Int. Cl.² ............................................ C07F 1/02
[58] Field of Search ............. 260/665 R; 252/431 L

[56] References Cited
UNITED STATES PATENTS

| | | | |
|---|---|---|---|
| 3,377,404 | 4/1968 | Zelinski | 260/665 R |
| 3,452,112 | 6/1969 | Kamienski et al. | 260/665 R |
| 3,541,176 | 11/1970 | Zuech | 260/680 B |
| 3,668,263 | 6/1972 | Morrison et al. | 260/665 R |
| 3,725,368 | 4/1973 | Morrison et al. | 260/84.7 |
| 3,776,964 | 12/1973 | Morrison et al. | 260/665 R |
| 3,862,251 | 1/1975 | Strecker | 260/665 R |

*Primary Examiner*—Paul M. Coughlan, Jr.
*Attorney, Agent, or Firm*—Wallenstein, Spangenberg, Hattis & Strampel

[57] ABSTRACT

Preparation of novel organotrilithium initiators, which are soluble in hydrocarbon media, from disubstituted vinylaromatic compounds and mono- and dilithium organic compounds, said initiators being useful in the polymerization of conjugated dienes and copolymerization of these with vinylaromatic compounds.

30 Claims, No Drawings

ORGANOTRILITHIUM POLYMERIZATION INITIATORS

This invention relates particularly to the preparation of novel organotrilithium initiators which are useful in polymerization processes. These initiators are soluble in hydrocarbon media, and are highly useful in the polymerization of conjugated dienes and vinyl-substituted aromatic compounds, and, also, in the preparation of novel functional prepolymers.

So far as we are aware, the hydrocarbon solvent-soluble organotrilithium polymerization initiators to which our invention relates have not been previously known or prepared. One particularly useful advantage of these initiators is that they make for ready preparation of functional prepolymers, e.g. hydroxyterminated polybutadienes (HTPB's), with functionalities greater than 2. These HTPB's can be readily cross-linked solely by the use of a diisocyanate curing agent, no polyfunctional isocyanate, of indeterminate functionality, being required. Another advantage is that the trifunctional initiators of our invention can be mixed with ordinary difunctional initiators in such proportions as to yield HTPB's having a range of functionalities (i.e. 2 to 3). A further advantage lies in the fact that strong Lewis bases (e.g. tetramethylethylenediamine (TMEDA) and tetrahydrofuran (THF)) are not needed to solubilize the organotrilithium initiators. This means that polymers prepared from these initiators have good elastomeric properties due to a high 1,4 microstructure which is generally not possible when such strong Lewis bases are used.

Still another advantage of the use of our novel initiators is that polymers of desired or predetermined molecular weights and possessing a narrow distribution of molecular weights (MWD) readily can be prepared. This is important because a narrow MWD leads to less viscous more easily processable polymers. Moreover, the polymers prepared from this initiator are true star polymers which are less viscous than conventional straight chain polymers of equivalent functionality prepared via heretofore known emulsion polymerization routes.

It should be understood that no novelty is claimed broadly in organotrilithium initiators or in their preparation, certain of such initiators being disclosed, for instance, in U.S. Pat. No. 3,377,404.

Generally speaking, our novel organotrilithium initiator compounds are made by mono-adducting a disubstituted vinylic aromatic compound, for instance, a divinyl benzene or a diisopropenyl benzene, with an organo mono-lithium compound, for instance, an alkyllithium such as sec-butyllithium, to form a mono-adduct, and then reacting said mono-adduct with an organodilithium compound to form the desired organotrilithium compound in solution. Alternatively, but less preferably, the disubstituted vinylic aromatic compound can be mono-adducted with the organodilithium compound and the resulting mono-adduct is then reacted with the alkyllithium.

In the preparation of the initial mono-adduct, various disubstituted vinylic aromatic compounds can be utilized, illustrative of which are 1,3-divinylbenzene; 1,4-divinylbenzene; 1,3-dipropenylbenzene; 1,3-diisopropenylbenzene; 1,4-diisopropenylbenzene; 2,4-diisopropenyltoluene; 2,4-divinyltoluene; the various divinylnaphthalenes; the various diisopropenylnaphthalenes; 1,3-distyrylbenzene; 1,4-distyrylbenzene; 1,2-distyrylbenzene; 1,3-diisobutenylbenzene; 1,3-diisopentenylbenzene; and the like.

The alkyllithium compounds used to prepare the monoorganolithium-divinyl- or diisopropenyl aromatic mono-adducts are generally in the $C_2$—$C_{12}$ range and include, for example, ethyllithium, n-propyllithium, isopropyllithium, n-butyllithium, isobutyllithium, sec-butyllithium, tert-butyllithium, n-amyllithium, isoamyllithium, sec-amyllithium, and tert-amyllithium. Of especially and preferred utility are secondary and tertiary alkyllithium compounds such as isopropyllithium, sec-butyllithium, tert-butyllithium, sec-amyllithium, and tert-amyllithium. Substituted alkyllithiums can also be used, such as aralkyllithium compounds, as, for example, benzyllithium, 1-lithioethylbenzene, and 1-lithio-3-methylpentylbenzene.

The organodilithium compounds employed in the production of the organotrilithium compounds of this invention include, by way of illustration and among others, 1,3- and 1,4-bis-(1-lithio-3methylpentyl) benzene, 1,3- and 1,4-bis-(1-lithio-1,3-dimethylpentyl) benzene, and the dilithio dimers of conjugated dienes such as isoprene, 1,4-hexadiene, 1,3-butadiene, 2,5-dimethyl-2,5-hexadiene, 2,3-dimethyl-1,3-butadiene, 1,3-pentadiene (piperylene), 2-methyl-3-ethyl-1,3-butadiene, and the like; as well as the $\alpha,\omega$-dilithioalkanes, such as 1,4-dilithiobutane, 1,5-dilithiopentane and the like.

The hydrocarbon solvent media which can be employed are normally liquid alkanes and cycloalkanes such as n-pentane, n-hexane, n-heptane and cyclohexane and normally liquid aromatic hydrocarbons, such as benzene, toluene, xylene, ethylbenzene and pseudocumene, as well as various mixtures of these types. The concentration range of the organotrilithium as prepared in solution can be varied widely, with solutions containing between 0.5 and 2 equivalents of C-Li per liter being most desirable.

Reaction temperatures utilized in the production of the trilithium initiators of the present invention are variable but, generally speaking, low temperatures are used, usually in the range of about −60° C to not substantially in excess of ambient temperatures, particularly desirably being temperatures in the range of about −30° C to 0° C.

In carrying out the initial preparation of the monoadduct, for instance from the disubstituted vinylic aromatic hydrocarbon and the alkyllithium, compound, the reaction medium may or may not include tertiary amines, notably monoamines. In the production of the organodilithium compound, and also in the subsequent step of reacting the mono-adduct with the organodilithium compound, tertiary amines should be present. The proportions of such amines, when utilized, are reasonably variable, Thus, it is desirable that said amines be present in proportions in a molar ratio range, based on C-Li, of about 0.5 to 1 to about 4 to 1, with a range of about 1 to 1 being most desirable, and a range higher than 1 to 1 being generally unnecessary. Triethylamine is especially satisfactory but various other tertiary amines, particularly monoamines, can be used as, for example, trimethylamine, tri-n-propylamine, triisopropylamine, ethyl di-n-propylamine, diethyl-n-butylamine, triisobutylamine, TMEDA; and arylalkyl tertiary amines illustrative of which are dimethylaniline, diethylaniline, diisopropylaniline and methylisobutylaniline.

As has been indicated from the foregoing descriptions, the mono addition of an alkyllithium compound to, for instance, a divinyl-substituted aromatic compound can be controlled to give exclusively, or essentially exclusively, a mono adduct, leaving intact one unreacted vinyl grouping which is then reacted with an organodilithium compound to give the novel hydrocarbon-soluble trifunctional initiators of our invention. Thus, for example, the addition of 1 molar equivalent of 1,3-diisopropenylbenzene to sec-butyllithium in hexane solution yields the mono-adduct, shown below:

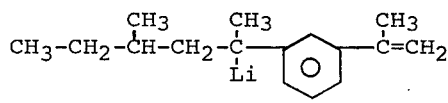

Then an organodilithium compound such as, for example, bis-(1-lithio-1,3-dimethylpentyl)benzene (formed by the addition of 1,3-diisopropenylbenzene to 2 molar equivalents of sec-butyl lithium) is added to the above mono-adduct solution to yield the desired organotrilithium compound, shown below:

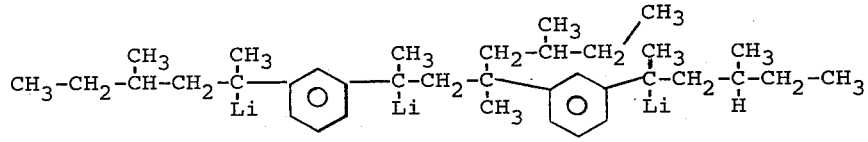

The monomers which can be polymerized in the presence of our aforementioned novel organotrilithium compounds are conjugated dienes containing from 4 to 12 carbon atoms, preferably 4 to 8 carbon atoms per molecule. Examples of these conjugated dienes include the following: 1,3-butadiene; isoprene; 2,3-dimethyl-1,3-butadiene; 1,3-pentadiene (piperylene); 2-methyl-3-ethyl-1,3butadiene; 3-methyl-1,3-pentadiene; 1,3-hexadiene; 2-methyl-1,3-hexadiene, and 3-butyl-1,3-octadiene. In addition, the above conjugated dienes containing various substituents along the chain can also be employed, as, for example, halogenated and alkoxy-substituted dienes such as chloroprene, fluoroprene; 2-methoxy-1,3-butadiene; 2-ethoxy-3-ethyl-1,3-butadiene and the like. Of the conjugated dienes, the especially preferred monomer is 1,3-butadiene, with isoprene and piperylene also being especially suitable. The conjugated dienes can be polymerized alone or in admixture with each other to form copolymers or by charging the dienes sequentially to form block copolymers.

In addition to the above-named conjugated dienes, other monomers can be copolymerized with these dienes including, by way of illustration, vinyl-substituted aromatic compounds such as styrene; 1-vinylnaphthalene; 2-vinyl naphthalene; and alkyl-cycloalkyl, aryl, alkaryl, alkoxy, aryloxy and dialkylamino derivatives thereof in which the total number of carbon atoms in the combined substituents is generally not greater than 12. Examples of such derivatives include 3-vinyltoluene; 4-phenylstyrene; 4- cyclohexylstyrene; 4p-tolylstyrene; 3,5-diphenylstyrene; 4-methoxystyrene; 4-dimethylamino-styrene; 3,5-diethylaminostyrene; 3-ethyl-1-naphthalene; 6-cyclohexyl-1vinyl-naphthalene; 6-benzyl-2-vinylnaphthalene; 4-methoxy-1-vinylnaphthalene; 6-phenoxy-1-vinylnaphthalene and the like. The vinyl-substituted aromatic compounds can be copolymerized with the conjugated dienes to form random or block copolymers. Generally, the presence, in the polymerization reaction medium, of trialkylamines, dialkylanilines, diarylethers and alkylarylethers in limited amount does not unduly affect the microstructure of the resulting polydiene polymers as does the presence of simple alkyl or cycloalkyl ethers such as diethyl ether or methyl cyclohexyl ether.

Polar monomers can be employed to form block copolymers with the conjugated dienes named. The polar monomer is charged after the conjugated diene has polymerized. Among the polar monomers applicable are vinylpyridines and vinylquinolines in which the vinyl group is positioned on a ring carbon other than a beta carbon with respect to the nitrogen. These pyridine, quinoline and isoquinoline derivatives can carry substituents such as alkyl, cycloalkyl, aryl, alkaryl, aralkyl, alkoxy, aryloxy and dialkylamino groups. The total number of carbon atoms in the combined substituents is generally not greater than 12. Also, there should be no primary or secondary alkyl groups on ring carbons in the alpha and gamma positions with respect to the nitrogen. Examples of these heterocyclic-nitrogen monomers are 2-vinylpyridine; 4-vinylpyridine; 3,5-diethyl-5-vinylpyridine; 5-cyclohexyl-2-vinylpyridine; 3-benzyl-4-vinylpyridine; 6-methoxy-2-vinylpyridine; 3,5-dimethyl-4-dimethyl-amino-2-vinylquinoline; 3-dimethylamino-3-vinylisoquinoline and the like. Still other polar monomers which can be utilized include acrylic and alkacrylic acid esters, nitriles, and N,N-disubstituted amides, such as methyl acrylate, methyl methacrylate, butyl methacrylate, acrylonitrile, methacrylonitrile, N,N-dimethylacrylamide, and N,N-diethylmethacrylamide, as well as vinylfuran and N-vinylcarbazole.

Our aforesaid novel organotrilithium initiators also can be used to prepare novel trifunctional polymers. This is done by adding a suitable capping agent, such as ethylene oxide, to the "living" polymer solution, as depicted in the equations as shown below:

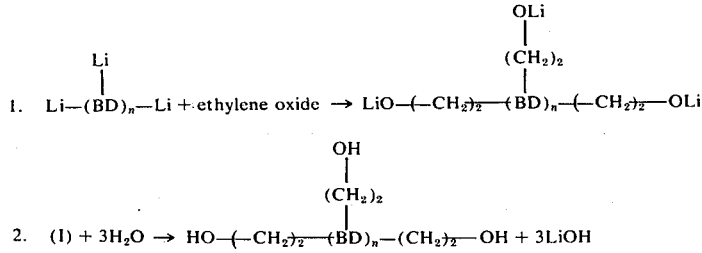

In these HTPB's, each hydroxy linkage is attached to its own butadiene chain in a star-shaped configuration:

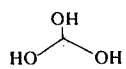

Such HTPB's differ from other so-called trifunctional HTPB polymers, which can be made via metalation of difunctional chains (prior to capping with ethylene oxide) in the presence of a strong Lewis base such as THF and a metalating agent such as sec-butyllithium.

The foregoing metalation is non-selective and occurs randomly among the chains yielding chains of varying functionality, i.e. 1,2,3,4 and on up, but having an average functionality of 3. As mentioned before, the said novel star HTPB's are generally less viscous than the metalated species and can readily cross-link solely by the use of a diisocyanate curing agent, no polyfunctional isocyanate of indeterminate functionality being required.

HTPB's containing chains of both di- and trifunctionality also can be prepared from a mixture of our novel trilithium initiators and known dilithium initiators. Surprisingly, gel permeation chromatography (GPC) traces of such HTPB's generally shows the molecular weight distribution to be very narrow, e.g. (MWD=1.13). This MWD is comparable to MWD's of HTPB's prepared either with the novel trilithium initiator or a conventional dilithium initiator. Also, the predetermined molecular weights (e.g. $\overline{M}_s$=5500) agree with the found molecular weight (e.g. $\overline{M}_n$=5600). calculated for the mixed system. Where mixtures of our novel trilithium initiators and heretofore known dilithium initiators are utilized in preparing HTPB's, the weight ratios of the trilithium to dilithium initiators will generally fall within the range of 90 to 10 to 10 to 90, and more particularly desirably about 65 to 35 to about 35 to 65. Examples of heretofore known dilithium initiators are shown in our U.S. Pat. No. 3,668,263.

Polymers containing active carbon-lithium bonds can be capped with various agents which convert these active carbon-lithium bonds to functional groupings. Examples of these capping agents are ethylene oxide, propylene oxide, styrene oxide, and the like. Also oxygen, carbon dioxide, ethyl benzoate, benzyl chloride, benzyl bromide, allyl chloride, alkyl chloride, allyl bromide, bromobenzene, p-bromoaniline, benzyl chloride, N-bromophthalimide, succinic anhydride, phthalic anhydride, p-amino benzoate, phosgene, thionyl chloride, phosphorus tribromide, ethyl adipate, ethyl sebacate, dibromo hexane, dibromo butane, bromonaphthalene, t-butyl bromide, t-butyl iodide, benzoyl chloride, bromine, iodine, tetrachloroethylene, Michler's ketone and other ketones, cyclic disulfides, 4-dimethylamino benzaldehyde and other aldehydes, sulfuryl chloride, carbon disulfide, chlorine, and sulfur dioxide can be used to provide additional examples of novel trifunctional polymers.

The following examples are illustrative of the production of organotrilithium and mixed organodi- and trilithium compositions and their use in polymerization reactions, all in accordance with the present invention. It will be understood that many other initiator compositions can be made and other polymerizations carried out in the light of the guidingg principles and teachings disclosed herein. All temperatures recited are guiding degrees Centigrade.

EXAMPLE I

Preparation of an Organotrilithium Compound via Interaction of 1,3-bis-(1-lithio-1,3-dimethylpentyl)benzene and 3-(1-lithio-1,3-dimethylpentyl)-alphamethylstyrene a. Preparation of 1,3-bis-(1-lithio-1,3-dimethylpentyl)benzene 3330 ml of 1.2N sec-butyllithium in hexane (4 moles) and 404 g of triethylamine (TEA) (4 moles) are charged to a 5-liter, 3-neck, round-bottom reaction flask. The reaction flask is equipped with stirrer, thermometer, addition funnel and a dry ice-hexane cooling bath. The flask and contents are cooled to −20° and premixed solution of DIPB (316 g — 2 moles) and 400 ml benzene are added dropwise over a period of 2 hours. The flask and contents are warmed to 30° and stirred for 1 hour.

b. Preparation of 3-(1-lithio-1,3-dimethylpentyl)-alphamethyl-styrene 316 g (2 moles) of 1,3-diisopropenyl benzene (DIPB) and 400 ml benzene are charged to a dry, argon flushed, 12-liter 3-neck, round-bottom reaction flask. The reaction flask is equipped with a stirrer, thermometer, addition funnel and a dry ice-hexane cooling bath. The flask and contents are cooled to −20° and a premixed solution of 1670 ml of a 1.2N sec-butyllithium in hexane (2 moles) and 202 g of TEA (2 moles) are added dropwise over a period of 2 hours. The temperature is held between −20° and −5° throughout the sec-butyllithium-TEA addition.

c. Preparation of Organotrilithium Compound

The dilithium compound of part (a) is added to the cold (−20°) monolithium adduct of part (b). The 12-liter flask and contents are then allowed to warm to ambient temperature. Stirring is continued for 12 hours. A volume of 7260 ml of a clear, deep red solution is obtained as the final product. The total alkalinity content is 0.825N, while the active carbon-lithium content is 0.825N (100% carbon-lithium active product). Gas chromatography analysis shows no sec-butyllithium or diisopropenylbenzene remaining in the solution. The product solution can be used directly as an initiator for the polymerization of conjugated dienes such as 1,3-butadiene.

EXAMPLE II

Preparation of a Mixed Organodi- and Trilithium Initiator Composition

Example I is repeated except that the quantity of sec-butyllithium used is 0.296 moles in preparing the mono-adduct of part (b), and 1.6 moles each of sec-butyllithium and TEA, and 0.8 moles of DIPB are used to prepare the organodilithium compound of part (a). When completed, the initiator consists of a 64:36 mole% mixture of di- and triorganolithium compounds. A volume of 2205 ml of a clear, deep red solution is obtained as the final product. The total alkalinity content is 0.86N, while the active carbon-lithium content is also 0.86N (100% carbon-lithium active product). Gas chromatography analysis shows no sec-butyllithium or diisopropenyl benzene remaining in solution.

The product solution can be used directly as an initiator for the polymerization of conjugated dienes such as 1,3-butadiene.

EXAMPLE III

Preparation of an Organotrilithium Compound via Interaction of the Dilithio Isoprene Dimer and 3-(1-lithio-1,3-dimethylpentyl)-alphamethylstyrene Example I (b) is repeated except that 0.58 moles each of sec-butyllithium, 1,3-diisopropenyl benzene, and TEA are used in preparing the mono adduct. A volume of 1290 ml of a 0.9N (active) DiLi-1 (dilithio-isoprene-dimer) solution in benzene is added to the mono-adduct above and the reaction mixture stirred overnight. A volume of 2029 ml of a clear, deep red solution is obtained as the final product. The total alkalinity content is 0.86N while the active carbon-lithium content is 0.85N (99% carbon-lithium lithium active product). Gas chromatography analysis shows no sec-butyllithium, DIPB or DiLi-1 remaining in solution.

The solution can be used directly as an initiator for the polymerization of conjugated dienes such as 1,3-butadiene.

EXAMPLE IV

Preparation of an Organotrilithium Compound via Interaction of 1,3-bis-(1-lithio-3-methylpentyl)benzene and 3-(1-lithio-3-methylpentyl)styrene Example 1 is repeated except that 0.492 moles each of 1,3-divinylbenzene (DVB) and sec-butyllithium are used to prepare the mono-adduct. No TEA is used in this step. Also, 0.984 moles each of sec-butyllithium and TEA along with 0.492 moles DVB are used to prepare the diadduct (organodilithium compound). A volume of 1622 ml of a clear, deep red solution is obtained as the final product. The total alkalinity content is 0.91N, while the active carbon-lithium content is 0.9N (99% carbon-lithium active product). Gas chromatography analysis shows no sec-butyllithium or DVB remaining in solution.

The above solution was used directly as an initiator for the polymerization of conjugated dienes such as 1,3-butadiene.

The following examples show the preparation of hydroxyl end-capped-polybutadienes utilizing the initiators of Example I and II.

EXAMPLE V

Conjugated Butadiene Polymer and Preparation of Hydroxyl-Terminated Polybutadiene Using a Trifunctional Initiator a. 2724 g of 1,3-butadiene and 20 liters of benzene are charged to a 10-gal polymerization reactor. A volume of 7260 ml (6.0 eq C-Li) of the 0.825N solution of the organotrilithium initiator of Example I are also added to the reactor. No precipitate occurs on addition of the initiator or during the ensuing 12-hour polymerization.

b. 2640 g (60 moles) of ethylene oxide are then added to the carbon-lithium containing polymer over a period of 2 hours. At this point the solution is completely gelled. After 2 hours the terminal lithoxy chain ends are converted to terminal hydroxy groups via the addition of a stoichiometric amount of $H_2O$. The resulting HTPB is then precipitated by addition of methanol and stripped of residual solvent under vacuum.

The HTPB is analyzed and has the following properties:

$\overline{M}_n$ = 2000 (predetermined number average molecular weight)
$\overline{M}_n$ = 2400 (actual number average molecular weight)
OH = 1.50 (predetermined hydroxyl number — meq/g)
OH = 1.16 (actual hydroxyl number — meq/g)
Hydroxyl Functionality = 2.6 (theoretical 3.0)
Viscosity = 141 poise at 25°C
Microstructure = 22% trans 1,4
44% cis 1,4 & sat
34% vinyl
Recovered Yield = 90%

EXAMPLE VI

Preparation of a Hydroxyl-Terminated Polybutadiene Using a Mixed Organodi- and Trifunctional Initiator Example V is repeated except that 3632 g 1,3-butadiene, 24 liters benzene, 2205 ml 0.86N initiator solution (from Example II) and 836 g ethylene oxide are employed. The resulting polymer has the following properties:

$\overline{M}_n$ = 5000 (predetermined number average molecular weight)
$\overline{M}_n$ = 5200 (actual number average molecular weight)
OH = 0.47 (predetermined hydroxyl number, meq/g)
OH = 0.42 (actual hydroxyl number, meq/g)
Hydroxyl Functionality = 2.18 (theoretical 2.35)
Viscosity = 106 poise at 25°C
Microstructure = 34% trans 1,4
37% cis 1,4 & sat
29% vinyl
Recovered Yield = 85%

EXAMPLE VII

Preparation of an Organotrilithium Compound via a Sequential Interaction of 1,3-Diisopropenylbenzene with 1,3-bis-(1-lithio-1,3-dimethylpentyl) benzene and Then sec-Butyllithium To 2 moles of 1,3-bis-(1-lithio-1,3-dimethylpentyl) benzene, prepared as in example I(a) above, is slowly added over a period of 2 hours at −20° a premixed solution of 1,3-diisopropenylbenzene (316 g — 2 moles) and 400 ml of benzene in a 12-liter flask. The mixture is stirred further for a period of 1 to 2 hours at −20° and then a premixed solution of 1670 ml of a 1.2N sec-butyllithium in hexane (2 moles) and 202 g of TEA (2 moles) are added dropwise over a period of 2 hours. The temperature is held between −20°and −5° throughout the sec-butyllithium-TEA addition, after which the flask and contents are allowed to warm to ambient temperature. Stirring is continued for 12 hours to insure complete reaction. The total alkalinity and active carbon-lithium contents are essentially equal at 0.83N.

We claim:

1. A process for preparing hydrocarbon solvent-soluble predominately organotrilithium compounds which comprises mono-adducting an aromatic hydrocarbon containing two vinylic groups with a monolithium compound which is an alkyllithium, or an aralkyllithium in which aralkyl radical is an unsubstituted hydrocarbon radical, and then subsequently reacting the remaining vinylic linkage with an organodilithium compound consisting solely of lithium, carbon and hydrogen and capable of adducting to activated unsaturated groupings.

2. A process according to claim 1 wherein said monolithium compound is a $C_4$—$C_5$ alkyllithium.

3. A process according to claim 2 wherein said $C_4$—$C_5$ alkyllithium is a secondary or tertiary alkyllithium.

4. A process according to claim 3 wherein said alkyllithium is sec-butyllithium.

5. A process according to claim 1 wherein said aromatic hydrocarbon containing two vinylic groups is diisopropenyl benzene.

6. A process according to claim 1 wherein said organodilithium compound is bis-(1-lithio-1,3-dimethylpentyl) benzene.

7. A process according to claim 4 wherein said aromatic hydrocarbon containing two vinylic groups is diisopropenyl benzene, and said organodilithium compound is bis-(1-lithio-1,3-dimethylpentyl) benzene.

8. A process for preparing hydrocarbon solvent-soluble predominately organotrilithium compounds which comprises mono-adducting an aromatic hydrocarbon containing two vinylic groups with an organodilithium compound consisting solely of lithium, carbon and hydrogen and capable of adducting to activated unsaturated groupings, and then subsequently reacting said mono-adduct with a monolithium compound which is an alkyllithium, or an aralkyllithium in which the aralkyl radical is an unsubstituted hydrocarbon radical.

9. A process according to claim 8 wherein said monolithium compound is a $C_4$-$C_5$ alkyllithium.

10. A process according to claim 9 wherein said $C_4$—$C_5$ alkyllithium is a secondary or tertiary alkyllithium.

11. A process according to claim 10 wherein said alkyllithium is sec-butyllithium.

12. A process according to claim 8 wherein said aromatic hydrocarbon containing two vinylic groups is diisopropenyl benzene.

13. A process according to claim 8 wherein said organodilithium compound is bis-(1-lithio-1,3-dimethylpentyl) benzene.

14. A process according to claim 11 wherein said aromatic hydrocarbon containing two vinylic groups is diisopropenyl benzene, and said organodilithium compound is bis-(1-lithio-1,3-dimethylpentyl) benzene.

15. A process for preparing hydrocarbon solvent-soluble predominately organotrilithium compounds which comprises reacting (a) an organodilithium compound consisting solely of lithium, carbon and hydrogen and capable of adducting to activated unsaturated groupings with (b) a mono-adduct of an aromatic hydrocarbon containing two vinylic groups with a monolithium compound which is an alkyllithium, or an aralkyllithium in which the aralkyl radical is an unsubstituted hydrocarbon radical, said mono-adduct containing substantially one free vinylic linkage.

16. A process according to claim 15 wherein said organodilithium compound is a member selected from the group consisting of 1,3- and 1,4-bis-(1-lithio-3-methylpentyl) benzene and (1-lithio-1,3-dimethylpentyl) benzene; dilithio dimers of $C_4$—$C_{12}$ conjugated dienes; and $\alpha,\omega$-dilithioalkanes.

17. A process according to claim 16 wherein said (b) ingredient is a mono-adduct of a divinyl- or diisopropenyl- benzene with an unsubstituted $C_4$—$C_5$ secondary or tertiary alkyllithium.

18. A process for preparing hydrocarbon solvent-soluble predominately organotrilithium compounds which comprises reacting- (a) an alkyllithium with (b) a mono-adduct of an aromatic hydrocarbon containing two vinylic groups with an organodilithium compound consisting solely of lithium, carbon and hydrogen and capable of adducting to activated unsaturated groupings.

19. A process according to claim 18 wherein said organodilithium compound is a member selected from the group consisting of 1,3- and 1,4-bis-(1-lithio-3-methylpentyl) benzene and (1-lithio-1,3-dimethylpentyl) benzene; dilithio dimers of $C_4$—$C_{12}$ conjugated dienes; and $\alpha,\omega$-dilithioalkanes.

20. A process according to claim 19 wherein said (b) ingredient is a mono-adduct of a divinyl- or diisopropenyl-benzene with a member selected from the group consisting of 1,3 and 1,4-bis-(1-lithio-3-methylpentyl) benzene and (1-lithio-1,3-dimethylpentyl) benzene; dilithio dimers of $C_4$—$C_{12}$ conjugated dienes; and $\alpha,\omega$-dilithioalkanes.

21. A composition containing predominately a hydrocarbon-solvent soluble organotrilithium initiator compound comprising a reaction product of (a) a mono-adduct of an aromatic hydrocarbon containing two vinylic groups with an alkyllithium with (b) an organodilithium compound consisting solely of lithium, carbon and hydrogen and capable of adducting to activated unsaturated groupings.

22. A compound according to claim 21 in which said mono-adduct is that of diisopropenyl benzene with an unsubstituted $C_4$—$C_5$ secondary or tertiary alkyllithium.

23. A composition containing predominately a hydrocarbon-solvent soluble organotrilithium initiator compound comprising a reaction product of (a) a mono-adduct of an aromatic hydrocarbon containing two vinylic groups with an organodilithium compound consisting solely of lithium, carbon and hydrogen and capable of adducting to activated unsaturated groupings with (b) a monolithium compound which is an alkyllithium, or an aralkyllithium in which the aralkyl radical is an unsubstituted hydrocarbon radical.

24. A compound according to claim 23 in which said monoadduct is that of diisopropenyl benzene with bis-(1-lithio-1,3-dimethylpentyl) benzene.

25. A compound according to claim 21 in which said alkyllithium is sec-butyllithium, and in which said organodilithium compound is a member selected from the group consisting of 1,3- and 1,4-bis-(1-lithio-3-methylpentyl) benzene and (1-lithio-1,3-dimethylpentyl benzene; dilithio dimers of $C_4$—$C_{12}$ conjugated dienes; and $\alpha,\omega$-dilithioalkanes.

26. A hydrocarbon solvent-soluble organotrilithium compound comprising the reaction product of 1,3-bis-(1-lithio-1,3-dimethylpentyl) benzene with 3-(1-lithio-1,3-dimethylpentyl)-alphamethylstyrene.

27. A hydrocarbon solvent-soluble organotrilithium compound comprising the reaction product of a dilithio isoprene dimer with 3-(1-lithio-1,3-dimethylpentyl)-alphamethylstyrene.

28. A composition containing predominately a hydrocarbon solvent-soluble organotrilithium compound comprising the reaction product of 1,3-bis-(1-lithio-3-methylpentyl) benzene and 3-(1-lithio-3-methylpentyl) styrene.

29. A compound according to claim 24 in which said alkyllithium is sec-butyllithium, and in which said organodilithium compound is a member selected from the group consisting of 1,3- and 1,4-bis-(1-lithio-3-methylpentyl) benzene and (1-lithio-1,3-dimethyl pentyl) benzene; dilithio dimers of $C_4$—$C_{12}$ conjugated dienes; and $\alpha,\omega$-dilithioalkanes.

30. A hydrocarbon solvent-soluble organotrilithium compound comprising the reaction product of sec-butyllithium with a mono-adduct of 1,3-bis-(1-lithio-1,3-dimethylpentyl) benzene with 1,3-diisopropenyl-benzene.

* * * * *